United States Patent
Adamo et al.

(10) Patent No.: US 8,538,707 B2
(45) Date of Patent: Sep. 17, 2013

(54) APPARATUS, SYSTEM AND METHOD FOR MEASURING RESISTANCE OF AN INHALER

(75) Inventors: Benoit Adamo, Mount Kisco, NY (US);
Scott McLean, Waterbury, CT (US);
Chad C. Smutney, Watertown, CT (US);
John M. Polidoro, Coventry, CT (US);
Carl R. Sahi, Coventry, CT (US)

(73) Assignee: MannKind Corporation, Valencia, CA (US)

( * ) Notice: Subject to any disclaimer, the term of this patent is extended or adjusted under 35 U.S.C. 154(b) by 654 days.

(21) Appl. No.: 12/722,464

(22) Filed: Mar. 11, 2010

(65) Prior Publication Data
US 2010/0235116 A1    Sep. 16, 2010

Related U.S. Application Data

(60) Provisional application No. 61/159,415, filed on Mar. 11, 2009.

(51) Int. Cl.
*G01F 1/34*    (2006.01)
*A61M 15/00*    (2006.01)

(52) U.S. Cl.
USPC ............................... 702/45; 128/203.12

(58) Field of Classification Search
USPC ............................................... 702/45
See application file for complete search history.

(56) References Cited

U.S. PATENT DOCUMENTS

| | | | | |
|---|---|---|---|---|
| 5,622,164 | A * | 4/1997 | Kilis et al. | 128/200.24 |
| 6,116,237 | A * | 9/2000 | Schultz et al. | 128/203.15 |
| 7,305,986 | B1 | 12/2007 | Steiner et al. | |
| 7,464,706 | B2 | 12/2008 | Steiner et al. | |
| 2009/0241949 | A1 | 10/2009 | Smutney et al. | |
| 2009/0308390 | A1 | 12/2009 | Smutney et al. | |
| 2009/0308391 | A1 | 12/2009 | Smutney et al. | |

OTHER PUBLICATIONS

Raid et al., Can all patients with COPD use the correct inhalation flow with all inhalers and does training help?, Jul. 12, 2007, pp. 2395-2401.*
Tuley et al., Experimental observations of dry powder inhaler dose fluidisation, Oct. 17, 2007, pp. 238-247.*
Mendes et al., A non-dimensional functional relationship for the fine particle fraction produced by dry powder inhalers, Apr. 2, 2007, pp. 612-624.*
Koning et al. Dry powder inhalation : technical and physiological aspects, prescribing and use, Chapter 3, 2001, pp. 43-56.*
Al-Showair et al. "Cann al patients with COPD use the correct inhalation flow with all inhalers and does training help?" Respiratory Medicine, vol. 101, No. 11, Oct. 9, 2007, p. 2395-2401.
International Search Report for PCT/US2010/027038 mailed Jun. 21, 2010.

* cited by examiner

*Primary Examiner* — Marc Armand
*Assistant Examiner* — Michael Dalbo
(74) *Attorney, Agent, or Firm* — K&L Gates LLP; Louis C. Cullman; Brian J. Novak

(57) ABSTRACT

An apparatus, a closed-loop system and method for measuring the resistance of inhalation systems and/or devices are disclosed.

14 Claims, 12 Drawing Sheets

ELECTRONIC BLOCK DIAGRAM FOR CLOSED LOOP RESISTANCE TEST SYSTEM

APPARATUS, SYSTEM AND METHOD FOR MEASURING RESISTANCE OF AN INHALER

CROSS REFERENCE TO RELATED APPLICATIONS

This application claims the benefit of U.S. provisional patent application No. 61/159,415, filed Mar. 11, 2009, the entire disclosure of which is incorporated herein by reference.

TECHNICAL FIELD

The present disclosure relates to a device, system and methods for measuring the resistance of inhalers to air flow. In particular, the apparatus and system can be used to measure the resistance to air flow of dry powder inhalers, which are used for pulmonary drug delivery.

BACKGROUND

Dry powder inhalers such as those described in U.S. Pat. Nos. 7,305,986, 7,464,706 and U.S. patent application Ser. No. 12/484,129 (2009/0308391), which disclosure is incorporated herein by reference in their entirety, can generate primary drug particles or suitable inhalation plumes during an inspiratory maneuver by deagglomerating the powder formulation within a container, capsule, or a cartridge. Dosing reproducibility requires that the drug formulation is uniform and that the dose can be delivered to the patient with consistent and reproducible results. Therefore, the dosing system must operate to completely discharge all of the formulation effectively during an inspiratory maneuver when the patient is taking his/her dose. The benefits of delivering drugs via the pulmonary circulation are numerous and include, rapid absorption into the arterial circulation, avoidance of drug degradation by liver metabolism, ease of use, i.e., lack of discomfort of administration, such as discomfort encountered by other routes of administration such as by injection.

The consistency in drug delivery from an inhaler is due in part to the consistency in resistance to air flow within the air passages of the inhalation device. High resistance dry powder inhalers such as those disclosed in U.S. Pat. Nos. 7,305,986 and 7,464,706, and U.S. patent application Ser. No. 12/484, 129 (2009/0308391), deliver drug formulations in a consistent manner. One of the parameters used to ascertain or predict if an inhaler would deliver a dose with consistency during use is by knowing the resistance to air flow of the device, which can be measured or determined after the device is manufactured.

Present systems and methods for measuring the resistance to air flow through an inhaler are cumbersome, involve numerous steps and calculations and are subject to variations in ambient conditions. Therefore, the inventors have seen the need to design and manufacture a simple apparatus, system, and method for measuring the resistance to airflow of an inhaler in order to determine if the inhaler resistance properties would render the inhaler suitable for use. The present system allows for a rapid method for measuring the resistance of inhalation systems or the individual inhalers, in an integrated system using a few simple steps.

SUMMARY

An apparatus, a system and a method for measuring the resistance of inhalation systems and/or devices are disclosed.

In embodiments described herein, the apparatus can comprise a pressure controller operably configured to a vacuum pump; a flow controller or flow regulator which is configured to connect to a positive air pressure generator; a first device comprising a first chamber and a second device comprising a second chamber; wherein the first chamber and the second chamber define an airflow pathway which can be sealed from ambient air when attached to one another in use; one or more pressure sensors, a flow rate sensor and one or more microprocessors, at least one microprocessor configured with the pressure controller and at least one microprocessor configured with the flow controller. In one embodiment, the apparatus comprises a first device and a second device each comprising a microprocessor configured to control a respective valve configured in their respective chamber and each microprocessor communicates information to a data acquisition board of a computer. In this and other embodiments, the first device also comprises a sensor configured to measure pressure differential between the chambers, and the second device comprises one or more sensors, for example, a laminar flow sensor configured to measure the flow rate of airflow within the chamber, and a pressure sensor configured to measure pressure differential across an inhaler. In one embodiment, the apparatus is configured so that the first device is firmly attached to a platform and the second device is mounted on at least one track so that it is movable on the track and sealably attachable to the first device. In one embodiment, the apparatus is configured to have an inhaler mounting adaptor.

A method for measuring the resistance to airflow of an inhaler is also provided, comprising: installing an inhaler on a holder of an apparatus comprising a vacuum pump; a flow controller or flow regulator which is configured to connect to a source of positive air pressure generator device; a first device comprising a first chamber and a second device comprising a second chamber; wherein the first chamber and the second chamber define an airflow pathway in a sealed system devoid of changes in environmental air pressure, and an inhaler with an air conduit in communication with the airflow pathway installed in the apparatus; measuring simultaneously the pressure differential across the inhaler and flow rate through the inhaler at predetermined pressures and flow rate settings in a controlled environment one or more times to generate pressure and flow rate measurements, and analyzing the pressure and flow rate measurements using an algorithm to determine the resistance value of the inhaler.

In one embodiment, the apparatus comprises a first device having a valve, a second device having a valve, a differential pressure sensor which communicates a first set of signals to a first microprocessor, the first microprocessor configured to control a valve of the first device which is integrally connected to a power source; a flow controller connected to the second device and comprising a laminar flow sensor and a pressure sensor which communicate a second set of signals with a second microprocessor; the second microprocessor configured to detect and analyze signals from the second chamber; the first microprocessor and the second microprocessor configured to control opening and closing of the valve corresponding to the first chamber and the second chamber; and a third microprocessor to read output from corresponding sensors output and an algorithm to analyze the measurements and calculate resistance to airflow of the inhaler. In one embodiment, the microprocessors can generate and analyze data from the first set of signals and the second set of signals that can be correlated to the resistance to airflow of an inhaler device being tested.

In another embodiment, a method for measuring the resistance to airflow of an inhaler is provided, the method comprising: attaching an inhaler in its dosing configuration to a first device comprising a first chamber and a holder for said inhaler so that an air pathway from the first chamber and through the inhaler air pathway to ambient air is formed; and said first chamber is closed to ambient air at its opposing end from the inhaler holder by the second chamber; simultaneously measuring pressure differential across the inhaler and flow rate through the inhaler in a controlled environment to generate pressure and flow rate measurements. In embodiments described herewith, the method of measuring the resistance of an inhaler is performed in a controlled environment at all times by a closed-loop algorithm and the pressure and flow rate measurements from various or multiple tests at predetermined set points are analyzed with an algorithm to generate a resistance value for the inhaler.

In one embodiment, an apparatus, comprising: a first device comprising a first chamber configured to mount an inhaler and having a first valve; a second device comprising a second chamber having a second valve; wherein the second device is movable and sealably attachable to the first device; a pressure controller connected to the first device, and comprising a pressure sensor which communicates a first set of signals to a first microprocessor and integrally connected to a power source; a flow controller connected to the second device and comprising a flow sensor and a pressure sensor which communicate a second set of signals with a second microprocessor configured to detect and analyze signals from the second chamber; and the first microprocessor and said second microprocessor configured to control opening and closing first valve and second valve, respectively and corresponding to the first chamber and the second chamber.

In this and other embodiments, the apparatus can further comprise a third microprocessor to read output from corresponding sensors output and implement an algorithm to analyze the measurements and calculate resistance values of the inhaler.

In another embodiment, the apparatus comprises a first device configured to hold an inhaler in place and create a seal between the first chamber and the second chamber of the second device. In one embodiment, the apparatus the first set of signals and the second set of signals generated by the first and second devices respectively, can generate data that when analyzed by a microprocessor are correlated to resistance to airflow of the device.

In another embodiment, the apparatus the apparatus in use to measure resistance to airflow of an inhaler is configured so that the first device and the second device are configured as a closed loop system devoid of ambient air.

In yet another embodiment, a method for measuring the resistance to airflow of an inhaler is provided, comprising: attaching an inhaler to a first device comprising a first chamber and a holder for said inhaler so that an air pathway from the first chamber and through the inhaler air pathway is formed; attaching a second device comprising a second chamber to said first device to enclose said inhaler within the second chamber; actuating the apparatus to obtain a controlled constant pressure environment in the second chamber; and simultaneously measuring pressure differential across the inhaler and flow rate through the inhaler to generate pressure and flow rate measurements. In this and other embodiments, the controlled constant pressure environment is maintained by a closed-loop algorithm of the apparatus in use, and wherein pressure and flow rate measurements from various test set points of the inhaler are analyzed with an alternate algorithm to generate a resistance value for the inhaler. In one embodiment, the resistance value for the inhaler is determined using measurement signals analyzed using a microprocessor. In alternate embodiments, the method for measuring resistance of the device measures pressure and flow rate at predetermined pressure drop settings for the inhaler.

In an alternate embodiment, a method for determining resistance to airflow of an inhaler, comprising: determining the range of measurements at which square root of the pressure differential versus flow rate curve for an inhaler type is linear to yield predetermined value settings; obtaining pressure differential and flow rate measurements at various predetermined value settings within the linear range for a second inhaler and determining the slope of the curve to obtain a resistance value for the inhaler. In this embodiment, the predetermined flow rate settings are greater than 0.1 L/min and at least three predetermined value settings are used to measure pressure differential and flow rate to determine the resistance value of the inhaler. In another embodiment, the method further comprises the step of measuring flow rate and square root of the pressure differential across an inhaler in an apparatus comprising a first chamber and a second chamber; wherein said inhaler is installed in the second chamber.

In another embodiment, the method comprises analyzing data obtained from pressure differential and flow rate measurements to obtain a linear regression of pressure and flow from data collected at least three predetermined value settings wherein the analysis results in a coefficient of determination greater than 0.9.

In an alternate embodiment, the apparatus can comprise a closed loop system comprising a single flow controller. In yet another embodiment, the apparatus can comprise a closed loop system comprising a single pressure controller and a flow meter. In this aspect, the apparatus can comprise a single chamber either around the inhaler or downstream from the inhaler. Measurements obtained from this system can be processed and analyzed similarly as with an apparatus comprising a dual chamber.

DETAILED DESCRIPTION

In embodiments disclosed herein, there is disclosed an apparatus, a system, and a method for measuring the resistance of an inhalation device. The apparatus provides several benefits to a user since it is a closed-loop system to control or eliminate environmental variables which can affect the resultant measurements and its ease of use provides a rapid system for assessing and determining the performance of an inhaler device during manufacturing. The apparatus is integrated with microprocessors and uses an algorithm in a computer system which facilitates data manipulation, analysis, storage and/or display of the measured parameters and calculated values in an automated manner. The apparatus and system are easy to use and resistance value data for an inhaler can be determined quickly with more accuracy due to the elimination of variation due to daily fluctuations in atmospheric pressure, thus significantly reducing errors in calculation. In other embodiments, the apparatus can also eliminate variables such as variations in air temperature and relative humidity. The apparatus can easily be configured to be adaptable to different inhaler design, can be made of different materials, including metals or high strength composites.

Figure 1:
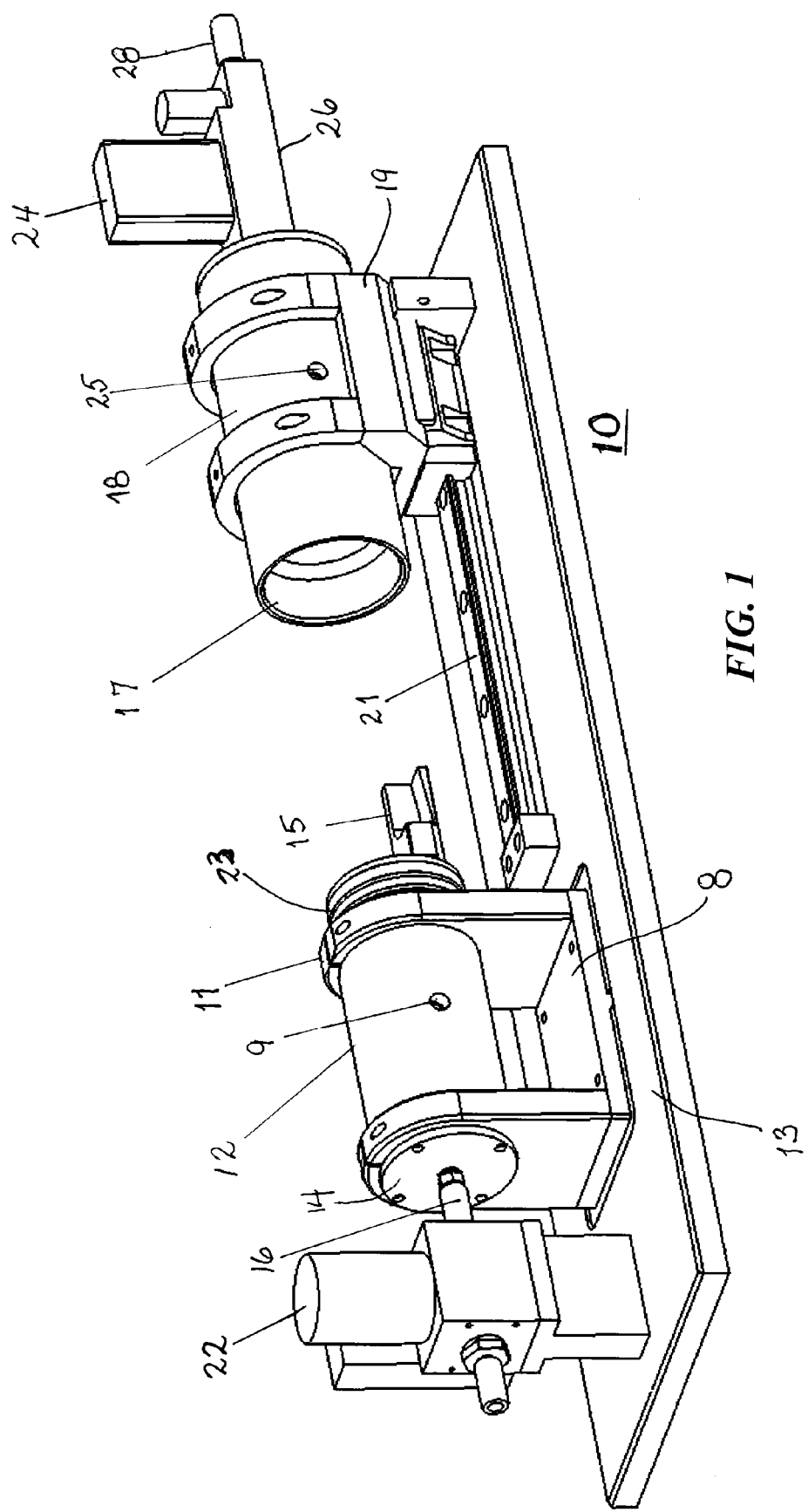
FIG. 1 depicts an isometric view of an embodiment of the apparatus for measuring the resistance of an inhaler.
Figure 2:
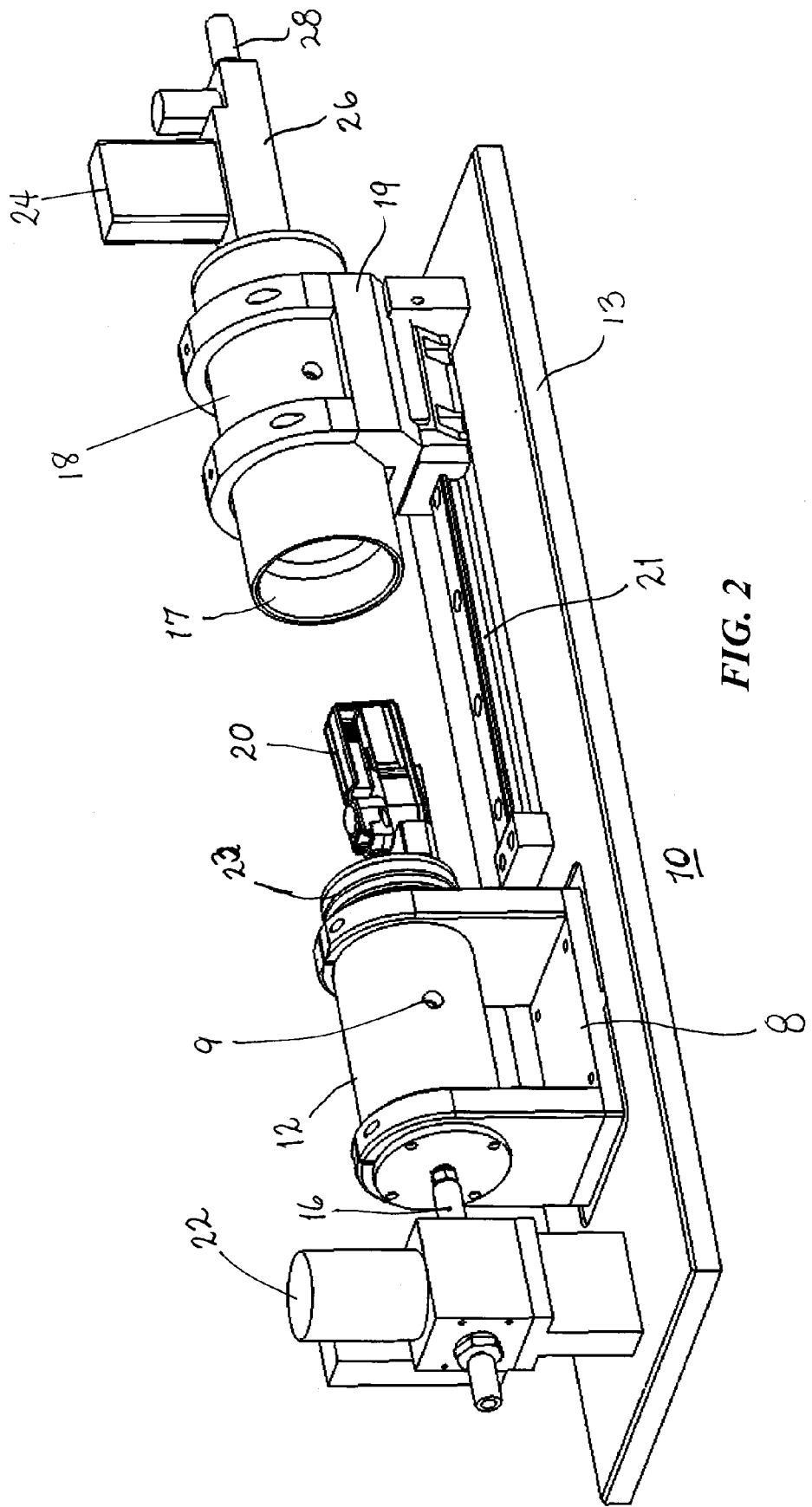
FIG. 2 depicts an isometric view of the embodiment illustrated in FIG. 1 with an inhaler in a dosing position mounted in the inhaler holder of the apparatus.

In one embodiment illustrated in FIGS. 1-7, the apparatus 10, comprises: a first device 11 mounted on a platform 13 by a mounting means, such as bracket 8 and comprising a first chamber 12 configured to have a holder 15 to mount an inhaler 20 (FIG. 2). The first device 11 is further provided with a cap 14 which has a central opening to allow a valve or tubing 16 to communicate with the interior of chamber 12. The first device 11 is configured to be adapted to a pressure pump (not shown) and is configured to be adapted or fitted with a second device 17 to form a contiguous body of the apparatus 10, wherein the first device and the second device 17 can form a seal to ambient air. The second device 17 comprises a mounting mechanism 19, such as a bracket 27 to hold the second chamber 18. The second device is also configured to be mounted or adapted to move on a track 21 attached to platform 13 so that the second device 17 is movable on a horizontal plane to meet and engage the first device 11.

In one embodiment, the first device 11 and the second device 17 are configured to have similar geometric shapes, such as a tubular configuration illustrated in FIGS. 1-7. The second device also comprises a second chamber 18 configured to engage chamber 12 to form a tight seal and enclose the inhaler mounting area 15. As illustrated in FIGS. 1 and 2, the first device comprises O-rings 23 at the end which engages the second device 17 to form the tight seal in excluding ambient air in use, and has an opening 9 configured to receive a tubing for communicating with sensors, such as pressure sensors in a pressure controller device 22. Inhaler holder or inhaler adaptor 15 can be configured in any shape or form so that any inhaler design can be adapted on the device. In embodiments herein, adaptor 15 can be made of any material that has sealable properties and an hold the inhaler in a dosing configuration.

Figure 3:
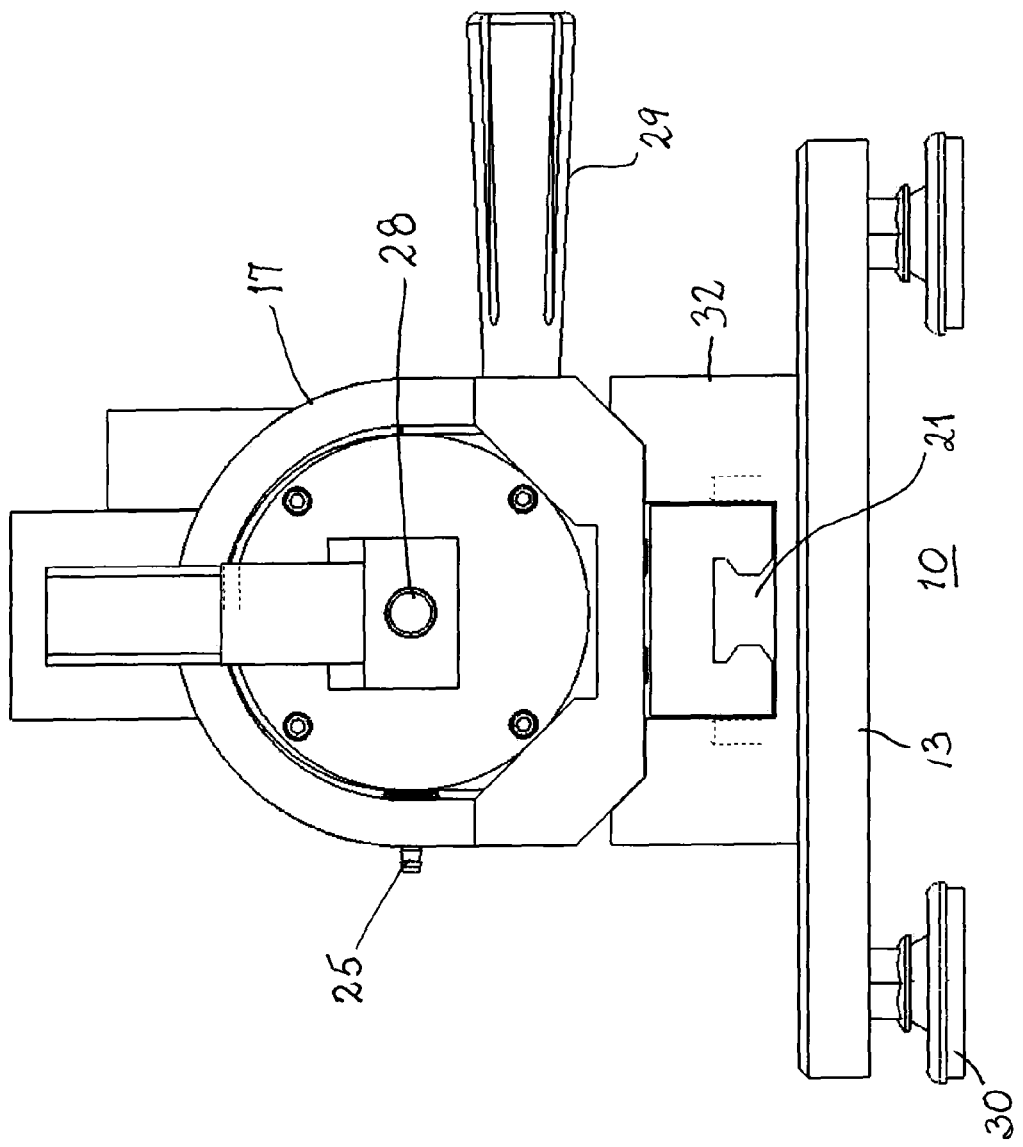
FIG. 3 depicts a side view of the embodiment illustrated in FIG. 1, showing the movable part of the apparatus having a handle for holding the device for moving on a track.

FIGS. 1-3 also depict the apparatus comprises a flow controller device 24 connected to the second device 17 by a mounting gear 26 configured with a conduit 28 to allow a tubing to be adapted to supply air flow or positive air pressure into the inside of chamber 18. The second chamber 18 is configured to have an opening 25 to allow the chamber 18 to communicate with a pressure sensor of the pressure controller 22 in measuring pressure differential between or across the two chambers 12, 18 in use. FIG. 3 depicts a side view of the second device 17 comprising a handle 29 which is configured for holding the device while moving on track 21. Handle 29 is configured to allow manual movement of the second device 17 on track 21. FIG. 3 also depicts that apparatus 10 can be provided with adjustable feet 30 attached to platform 13 so that the apparatus can be balanced in a horizontal plane; and wherein the feet can be provided with a shock absorbing system to prevent vibration of the instrument during use.

Figure 4:
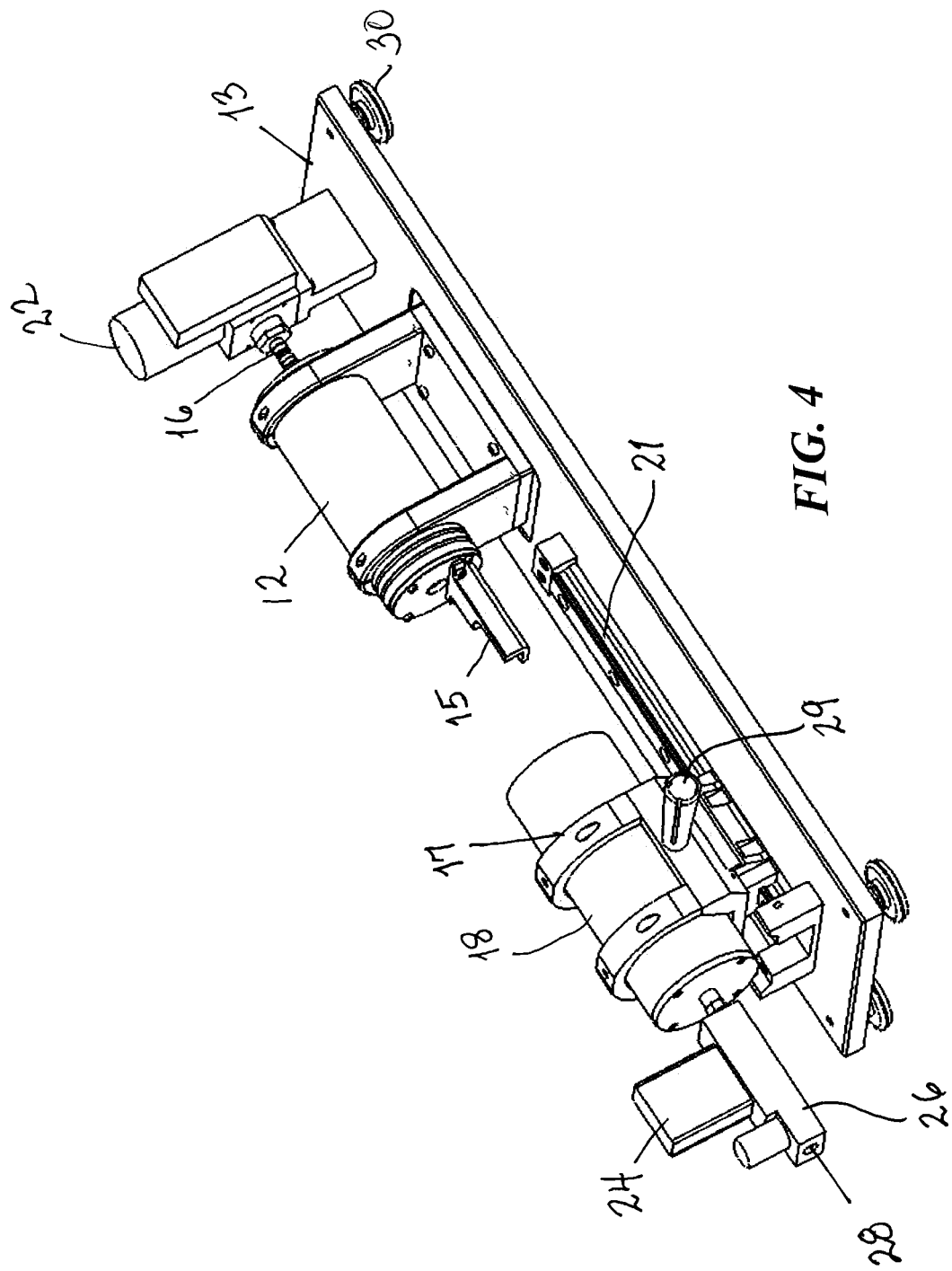
FIG. 4 depicts a perspective view of the front of the apparatus illustrated in FIG. 1 prior to use.
Figure 5:
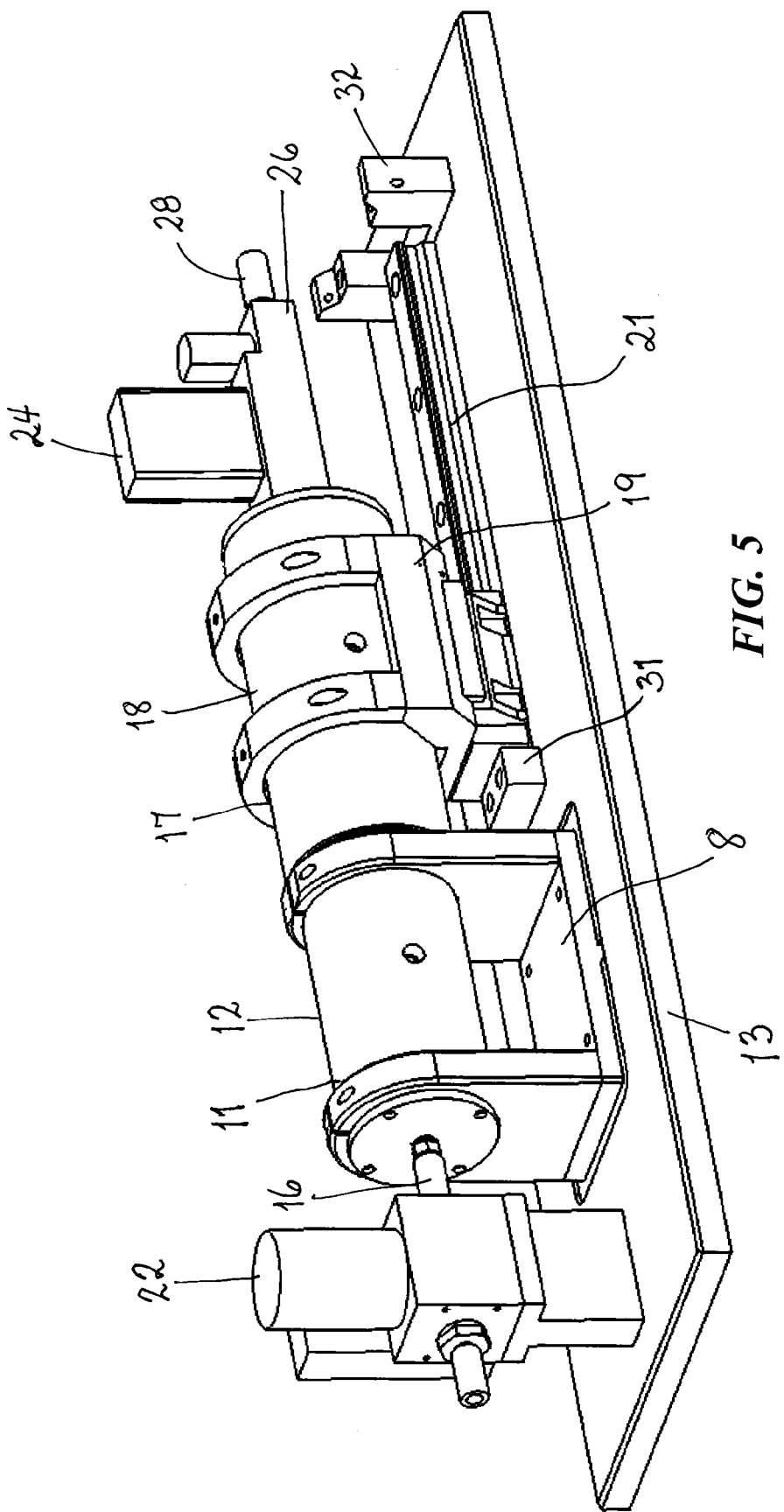
FIG. 5 depicts the apparatus illustrated in FIG. 1 in a closed, and sealed, configuration or in use.
Figure 6:
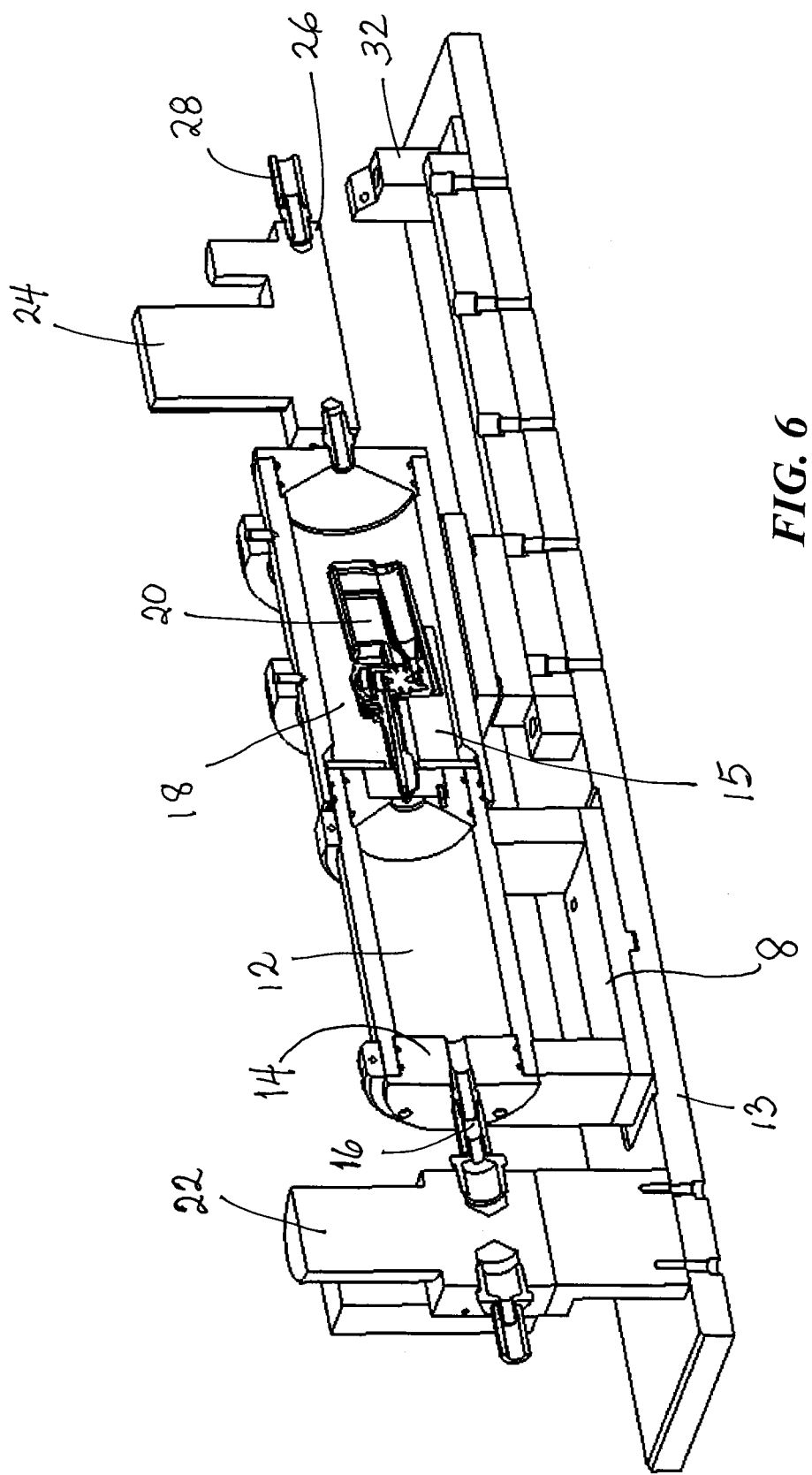
FIG. 6 depicts a perspective view of the apparatus illustrated in FIG. 5 in cross-section through its longitudinal axis with an inhaler installed in the apparatus.
Figure 7:
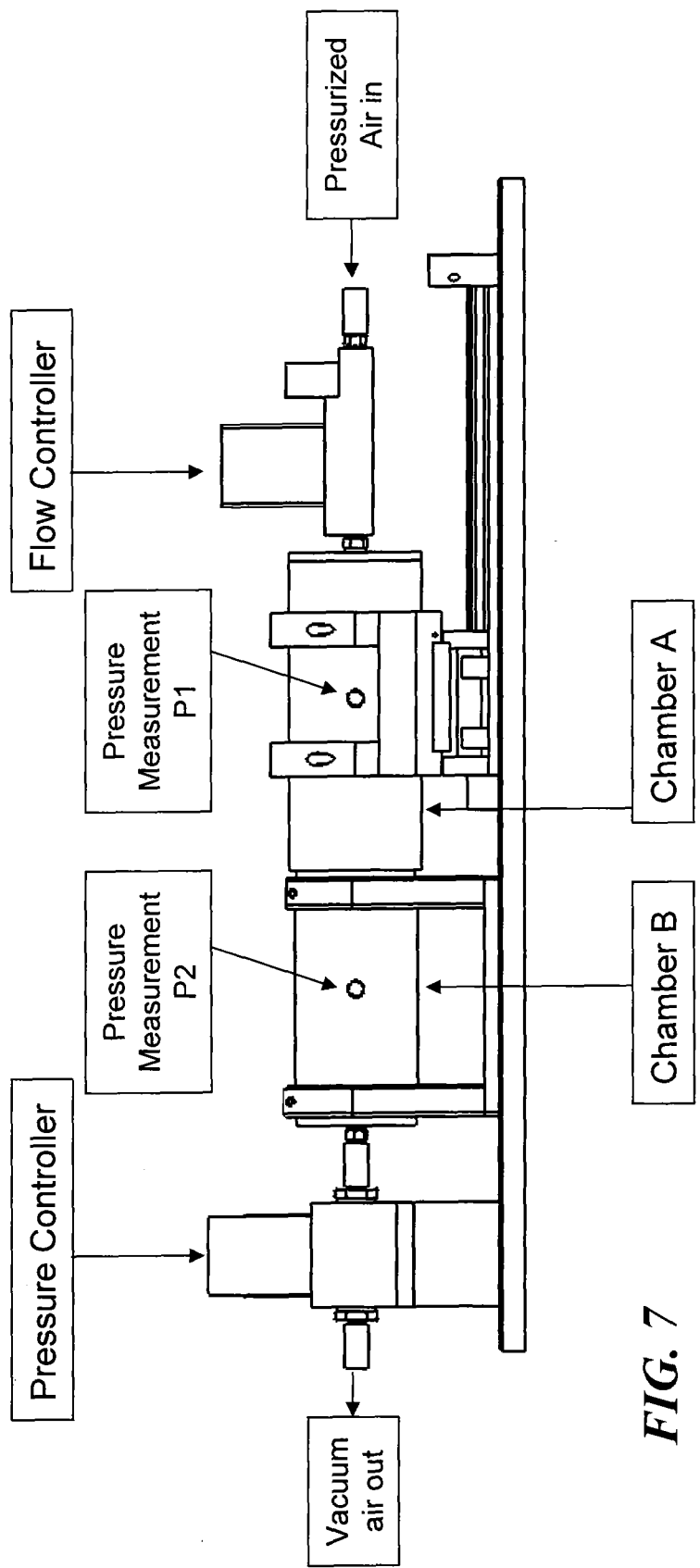
FIG. 7 depicts a side view of the embodiment in FIG. 5 illustrating the various component parts of the apparatus.

FIG. 4 depicts a front, isometric view of the apparatus showing the position of handle 29 on mounting gear 19 of second device 17. FIGS. 5-7 depict the apparatus in an in use configuration wherein first device 11 and second device 17 are engaged and second device 17 is prevented from moving by a stopping mechanism, for example, a block 31 at the end of the track 21 proximal to first device 11. A second stop block 32 at the distal end of track 21 can also be provided to prevent second device 17 from falling off track 21. FIG. 6 depicts a cross-section of the embodiment described in FIGS. 1-5 through its mid-longitudinal axis of the apparatus showing a MEDTONE® inhaler mounted on the first device and enclosed within second chamber 17.

Figure 8:
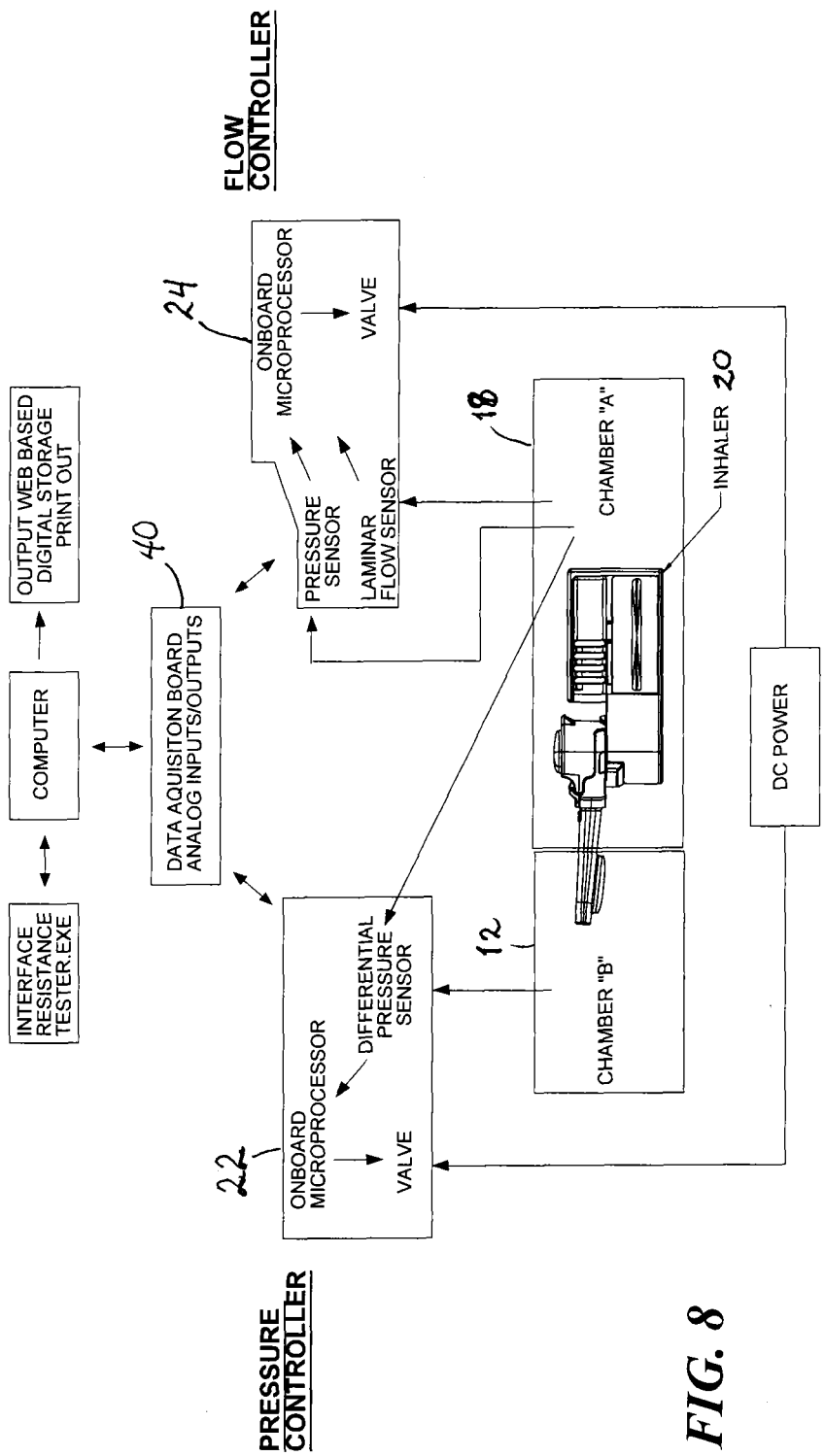
FIG. 8 illustrates a block diagram of the electronics associated with the resistance measuring apparatus and system.

FIG. 7 depicts a schematic representation of the components parts of the apparatus which facilitate the measurement of the resistance of an inhaler device and FIG. 8 illustrates an electronic block diagram of an embodiment of the closed-loop resistance test system described herewith. FIGS. 7 and 8 also shows the apparatus comprises a pressure controller 22 comprising a valve, a microprocessor, which integrates and analyzes signals from one or more sensors, for example, pressure sensors which detect signals in chambers 12, 18, for example, pressure differential across the chambers to the data acquisition board 40. The microprocessor in the pressure controller 22 also receives signals from the data acquisition board 40 to regulate the opening and closing of the valve to pressurize or depressurize the chambers as needed. Apparatus 10 also comprises a power source and it is integrated in a system with a data acquisition board 40 which communicates data to a computer equipped with control software for human to machine interface. The system can also have capabilities to provide output as web based, digital storage, print out and the like.

FIG. 8 also shows that the apparatus also comprises a flow controller 24 comprising a microprocessor, a laminar flow sensor, a valve, and a pressure sensor. The microprocessor in the flow controller 24 regulates opening and closing of the valve to regulate airflow into second chamber 18, and integrates and analyzes signals from chamber 18 and communicates signals to and from the data acquisition board 40 for integration and response. The data acquisition board 40 can receive and send data as analog signals.

FIG. 8 depicts how the closed-loop resistance test system is electronically integrated. In one embodiment, and during operation, the apparatus can measure pressure across an inhaler and rate of airflow through that inhaler simultaneously.

In embodiments herewith, a method for measuring the resistance of an inhaler to air flow due to the geometries of the air conduits of the inhaler is disclosed; wherein the method comprises installing or adapting an inhaler in a dosing configuration into the apparatus; creating an air pathway between the inhaler and a first device and a second device of the apparatus by making a seal to ambient environment and forming a first chamber and a second chamber; actuating a vacuum pump connected to the apparatus so that pressure in the first chamber is maintained at one atmosphere; measuring the pressure differential across the first chamber and second chamber when the flow rate of a gas into the chamber is set at varying predetermined values to obtain data; and analyzing the data obtained and determining the resistance to airflow of the inhaler. In one embodiment, once the linear range of the curve for pressure drop versus flow rate is determined based on the Bernoulli principle for a particular inhaler type, the resistance to airflow of other inhalers having similar geometric air conduits can be measured at predetermined values of within the linear range of the curve.

In one embodiment, the predetermined values of flow rates setting vary for the inhaler type and can be assessed for each inhaler after multiple tests to attain a linear range for pressure versus flow rate. The apparatus disclosed herein can be used at various flow rates setting depending on the inhaler internal air conduits. In one embodiment, flow rate settings can be greater than 0.1 L/min. In another embodiment, the flow rate settings can range from about 3 L/min to about 60 L/min. In another embodiment, the apparatus can be used a varying pressure drops depending on the inhaler design. Predetermined pressure drop value settings can be greater than 0.1 $kPa^{1/2}$.

While the apparatus describe above and in the examples below perform measurements through microprocessor controlled systems, in alternate embodiments, the system can operate with other types of control systems such as mechanical.

EXAMPLE 1

Measuring the Resistance of Dry Powder Inhalers

Three different dry powder inhaler designs manufactured by MannKind Corporation were used in these experiments, including the MEDTONE® inhaler and two other designs disclosed in U.S. patent applications Ser. Nos. 12/413,405 (US 2009/0241949); 12/484,129 (US 2009/0308391) and 12/484,125 (US 2009/0308390), which disclosures are incorporated herein by reference as they pertain.

To measure the resistance of the each inhaler, the inhaler in the dosing configuration was placed or mounted to the first chamber. The dosing configuration forms an air pathway through the inhaler air conduits and through the cartridge in the inhaler. The second device is moved so that it engages the first device. The system is actuated and the vacuum pump evacuates the first chamber so the pressure is maintained at approximately one atmosphere (1 atm) at all times. Other pressure settings can be applied depending on the inhaler to be tested. Airflow is then provided at different settings and multiple times so the system can measure the pressure across the inhaler and airflow rate through the inhaler. The data is then analyzed and graphed for the desired parameters.

Figure 9:
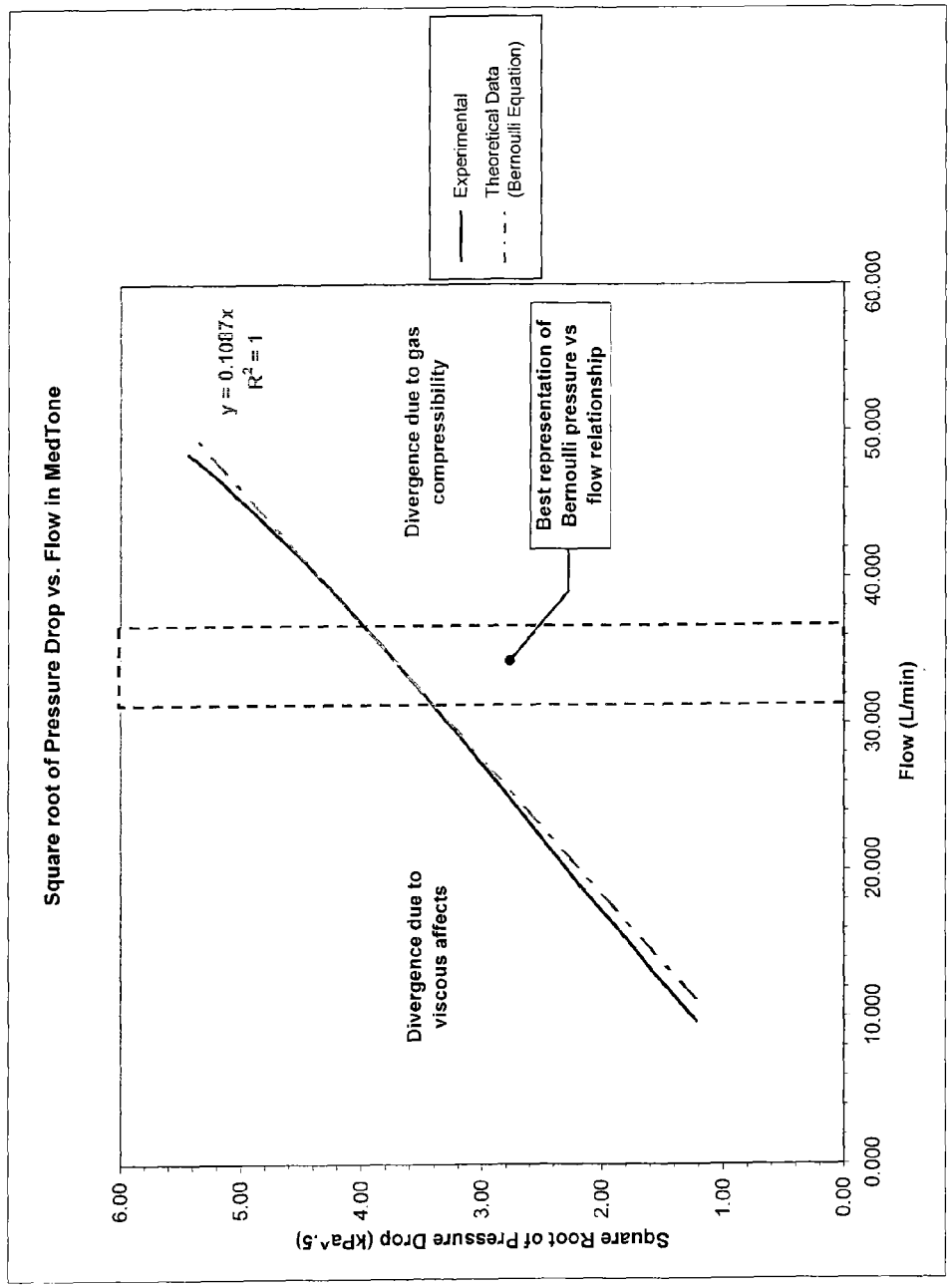
FIG. 9 is a graphic representation of an inhaler performance test using an apparatus described herein compared to theoretical values. The data are plotted as flow rate in the x-axis versus pressure differential for a MEDTONE® inhaler prototype.
Figure 10:
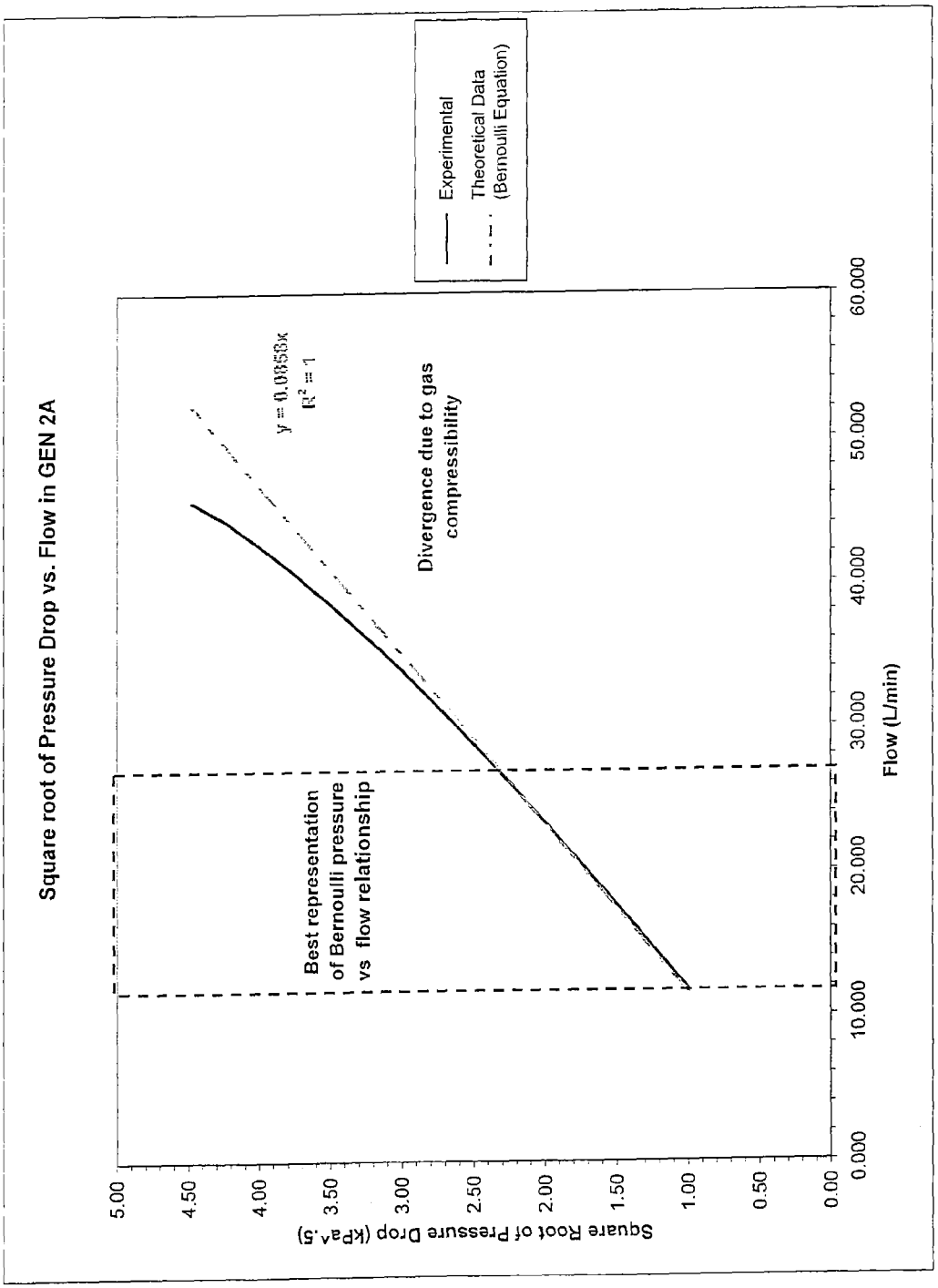
FIG. 10 is a graphic representation of an inhaler performance test using an apparatus described herein compared to theoretical values. The data are plotted as flow rate in the x-axis versus pressure differential for an alternate inhaler design.
Figure 11:
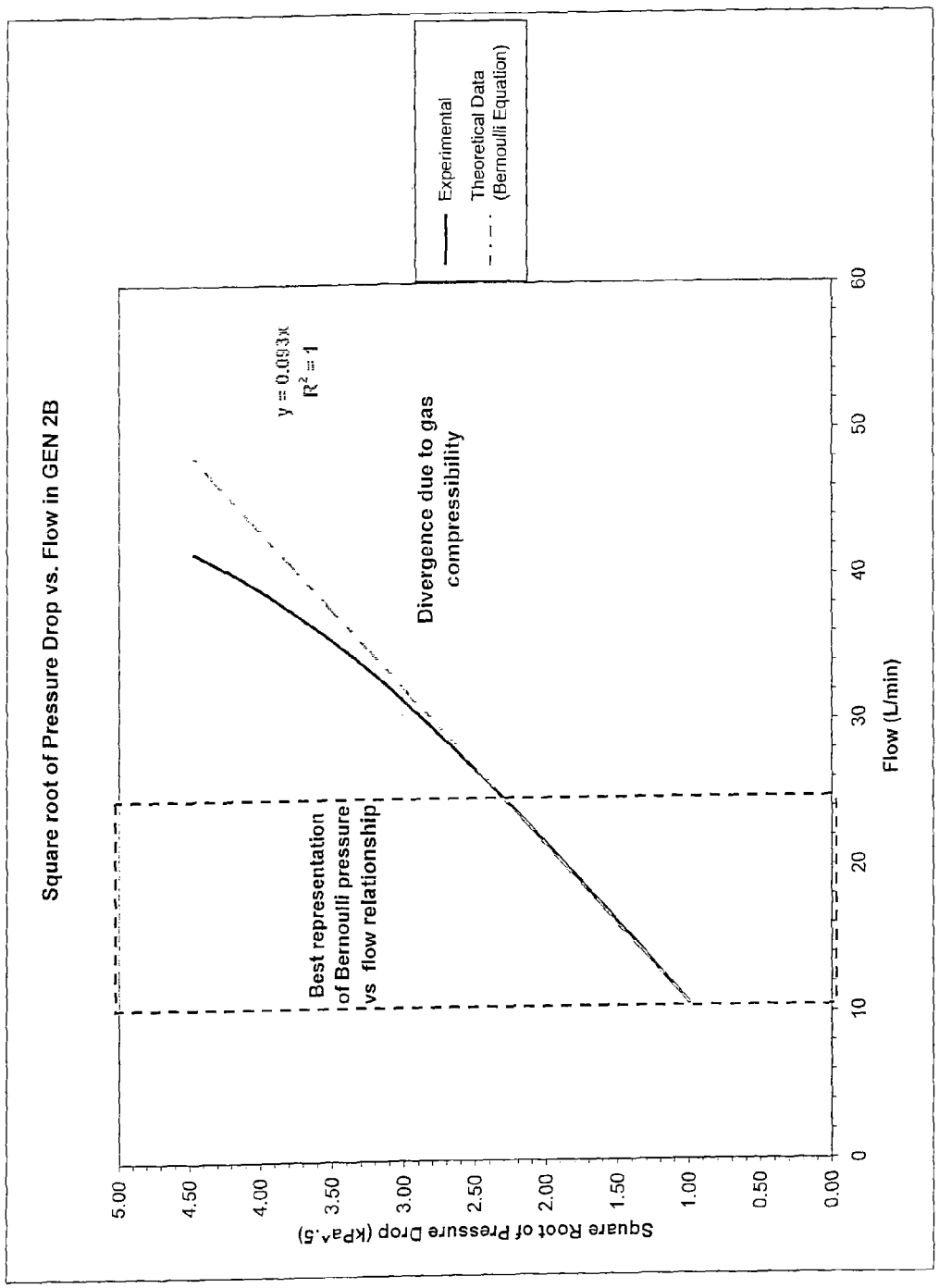
FIG. 11 is a graphic representation of an inhaler performance test using an apparatus described herein compared to theoretical values. The data are plotted as flow rate in the x-axis versus pressure differential for yet another inhaler design.

Since different inhaler designs exhibit different resistance values due to the different geometries of their air pathways, multiple experiments were conducted to determine the ideal interval for pressure settings to use with each particular design. Based on the Bernoulli principle, and only where linearity exists between the square root of pressure and flow rate, the linearity intervals were predetermined for the three inhalers used after multiple tests so that the appropriate settings could be used with other batches of the same inhaler design, having the same geometric configurations of their air pathways. FIGS. 9, 10 and 11 are graphs of measurements of pressure and flow rates made, respectively, for MEDTONE® (FIG. 2, 20), and two other inhaler prototypes. The numbers are averages of multiple measurements from multiple inhalers. FIG. 9 depicts a graph of the measurements of flow rate in liters/minute (L/min) in the x-axis versus square root of pressure differential ($kPa^{1/2}$) for MEDTONE®, showing that the interval for measuring the resistance of this inhaler prototype falls at a flow rate of about 30 L/min to about 40 L/min at pressure differentials of about 3.2 to about 4 square root of pressure drop ($kPa^{1/2}$). FIG. 10 depicts a graph of the measurements made with a second inhaler prototype (GEN 2A), which shows that for this design, the predetermined interval which reflects linearity of pressure and flow rate was for flow rates from about 10 L/min to about 28 L/min and for pressure differential of from about 1 kPa to about 2.3 $kPa^{1/2}$. FIG. 11 shows a graph for the third inhaler prototype (GEN 2B), in which the interval reflecting linearity was determined to be between about 1 $kPa^{1/2}$ and 2.3 $kPa^{1/2}$, similarly as the GEN 2A inhaler.

EXAMPLE 2

Resistance test measurements were made with settings within the predetermined Bernoulli interval for three different inhaler designs for different batches of the respective inhalers using the apparatus and system described herewith. All three tests were conducted at flow rates and pressure drops established by their respective intervals or wherein linearity was attained for the inhaler type tested. Three predetermined settings were used and measurements were made multiple times for each inhaler as follows. The inhaler is installed in the holder, the vacuum is turned on and the apparatus is closed to ambient air. The system can operate automatically as follows with reference to FIG. 7:

System start-up and stabilization: The pressure controller valve is opened to achieve the first set point, i.e., pressure differential across the inhaler, which is equal to absolute pressure in Chamber A (FIG. 7) (i.e. first chamber 12; FIGS. 1-6) minus absolute pressure in Chamber B (i.e. second chamber 18; FIGS. 1-6). The pressure in Chamber A is then maintained at 1 atmosphere and the system is allowed to stabilize for approximately 10 seconds. The system then measures pressure and flow rate of an inhaler at three different settings (Test conditions):

Test condition 1: The pressure drop and flow rate through the inhaler is measured 10 times during which the pressure differential between Chamber A and Chamber B is within 5% of the set point, which set point is determined by the inhaler design. Each time the pressure controller records a pressure drop measurement, the flow controller records a flow rate measurement so that 10 pressure and 10 flow rate values are measured.

Test condition 2: The pressure is adjusted by the pressure controller valve to achieve the second set point pressure drop across the inhaler and the Chamber A pressure is maintained at approximately 1 atmosphere until the system is stabilized.

Pressure drop and flow rate through the inhaler are measured again 10 times during which the pressure differential is within 5% of the set point. Again, each time the pressure controller records a pressure drop measurement, the flow controller also records a flow rate measurement and thus 10 pressure and corresponding flow rate values are obtained.

Test condition 3: The pressure controller valve is once again adjusted to achieve the third set point pressure drop across the inhaler. Again, Chamber A is maintained at approximately one atmosphere and the system is allowed to stabilize. The pressure drop between the chambers and flow rate through the inhaler are measured 10 times to obtain 10 more pressure and flow rate measurements.

Calculations: The average of the pressure drop values and corresponding flow rate conditions from each of the test conditions is determined and plotted as the square root of pressure drop versus flow rate for all three conditions. A linear regression of the data is performed to force the curve through the origin and the slope of the linear regression plot is equal to the resistance value of the inhaler tested. The coefficient of determination of this linear regression is also calculated to confirm that no irregularities occurred during testing. The $R^2$ value must exceed 0.990 for the inhalers tested.

Figure 12:
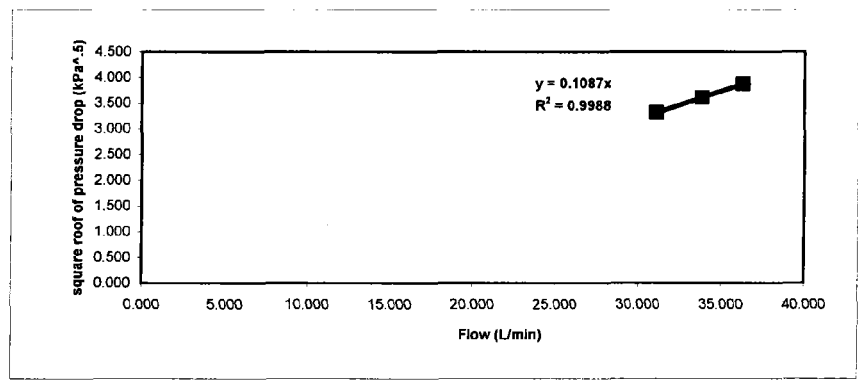
FIG. 12 depicts a graph showing the pressure differential and flow rate measurements from the data depicted in FIG. 9 for a MEDTONE® inhaler prototype and the calculated resistance value for the inhaler tested.
Figure 13:
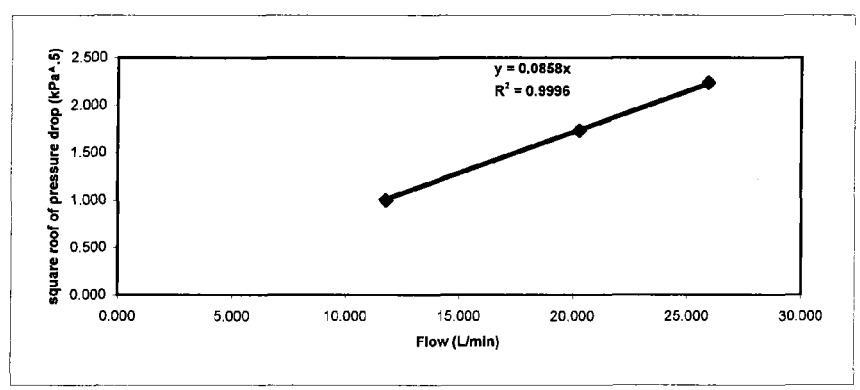
FIG. 13 also depicts a graph showing the pressure differential and flow rate measurements from the data depicted in FIG. 10 for a second inhaler prototype and the calculated resistance value for the inhaler tested.
Figure 14:
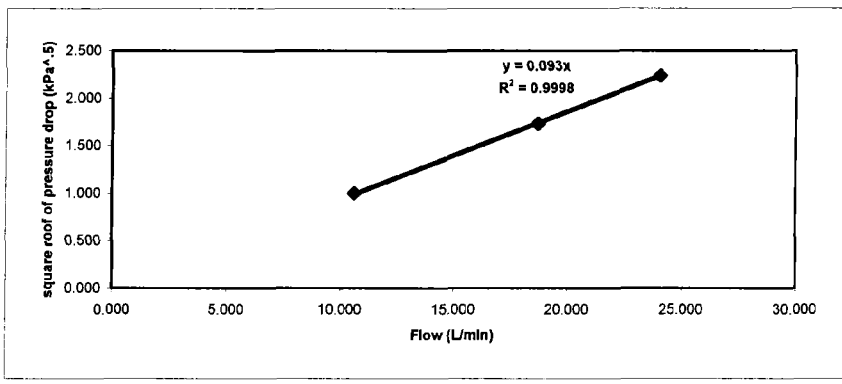
FIG. 14 also depicts a graph showing the pressure differential and flow rate measurements from the data depicted in FIG. 11 for a third inhaler prototype and the calculated resistance value for the inhaler tested.

FIGS. 12, 13 and 14 are graphs showing data of measurements made from the three different inhalers using the apparatus described herewith. FIG. 12 depicts data exemplary of a MEDTONE® inhaler showing the function and the coefficient of determination quantifying the linear regression. As seen in the graph, the resultant value for this inhaler was determined as 0.1087 $(\sqrt{kPa})/L$ per minute. FIG. 13 depicts data exemplary of a second (GEN 2A) inhaler showing the function and the coefficient of determination quantifying the linear regression. As seen in the graph, the resultant value for this inhaler was determined as 0.0858 $(\sqrt{kPa})/L$ per minute. FIG. 14 depicts data exemplary of a third (GEN 2B) inhaler showing the function and the coefficient of determination quantifying the linear regression. As seen in the graph, the resultant value for this inhaler was determined as 0.093 $(\sqrt{kPa})/L$ per minute.

The preceding disclosures are illustrative embodiments. It should be appreciated by those of skill in the art that the techniques disclosed herein elucidate representative techniques that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. All references cited in this specification, and their references, are incorporated by reference herein in their entirety where appropriate for teachings of additional or alternative details, features, and/or technical background.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An apparatus, comprising:
  a first device comprising a first chamber configured to mount an inhaler and having a first valve;

a second device comprising a second chamber having a second valve; wherein said second device is movable and sealably attachable to said first device;

a pressure controller connected to said first device, and comprising a pressure sensor which communicates a first set of signals to a first microprocessor and integrally connected to a power source;

a flow controller connected to said second device and comprising a flow sensor and a pressure sensor which communicate a second set of signals with a second microprocessor configured to detect and analyze signals from said second chamber; and said first microprocessor and said second microprocessor configured to control opening and closing first valve and second valve, respectively and corresponding to said first chamber and said second chamber.

2. The apparatus of claim 1, further comprising a third microprocessor to read output from corresponding sensors output and implement an algorithm to analyze the measurements and calculate resistance values of the inhaler.

3. The apparatus of claim 1, wherein said first device is configured to hold an inhaler in place and create a seal between the first chamber and the second chamber of the second device.

4. The apparatus of claim 1, wherein the first set of signals and the second set of signals generate data that when analyzed are correlated to resistance to airflow of the device.

5. The apparatus of claim 1, wherein the apparatus is used to measure resistance to airflow of an inhaler when the first device and the second device are configured as a closed loop system devoid of ambient air.

6. A method for measuring the resistance to airflow of an inhaler, comprising:

attaching an inhaler including an inhaler air pathway to a first device comprising a first chamber, a first valve, a pressure controller including a pressure sensor which communicates a first set of signals to a first microprocessor and integrally connected to a power source, and a holder for said inhaler so that an air pathway from the first chamber and through the inhaler air pathway is formed;

attaching a second device comprising a second chamber to said first device to enclose said inhaler within the second chamber, wherein the second device includes a second valve and a flow controller comprising a flow sensor and a pressure sensor which communicate a second set of signals to a second microprocessor configured to detect and analyze signals from said second chamber;

actuating the apparatus to obtain a controlled constant pressure environment in the second chamber; and simultaneously measuring pressure differential across the inhaler and flow rate through the inhaler by controlling opening and closing of the first valve and the second valve by said first microprocessor and said second microprocessor respectively to generate pressure and flow rate measurements.

7. The method of claim 6, wherein the controlled constant pressure environment is maintained by a closed-loop algorithm.

8. The method of claim 6, wherein pressure and flow rate measurements from various test set points of the inhaler are analyzed with an algorithm to generate a resistance value for the inhaler.

9. The method of claim 8, wherein the pressure and flow rate measurements are made at predetermined pressure drop settings for the inhaler.

10. A method for determining resistance to airflow of an inhaler, comprising:

attaching an inhaler including an inhaler air pathway to a first device comprising a first chamber, a first valve, a pressure controller including a pressure sensor which communicates a first set of signals to a first microprocessor and integrally connected to a power source, and a holder for said inhaler so that an air pathway from the first chamber and through the inhaler air pathway is formed;

attaching a second device comprising a second chamber to said first device to enclose said inhaler within the second chamber, wherein the second device includes a second valve and a flow controller comprising a flow sensor and a pressure sensor which communicate a second set of signals to a second microprocessor configured to detect and analyze signals from said second chamber;

actuating the apparatus to obtain a controlled constant pressure environment in the second chamber;

determining a range of measurements at which square root of the pressure differential versus flow rate curve for an inhaler type is linear to yield predetermined value settings;

obtaining pressure differential and flow rate measurements by controlling opening and closing of the first valve and the second valve by said first microprocessor and said second microprocessor respectively at various predetermined value settings within the linear range for a second inhaler and; and determining the slope of the curve to obtain a resistance value for the inhaler.

11. The method of claim 10, wherein the predetermined flow rate settings are greater than 0.1 L/min.

12. The method of claim 10, wherein at least three predetermined value settings are used to measure pressure differential and flow rate and determine the resistance value of the inhaler.

13. The method of claim 10, further comprising the step of measuring flow rate and square root of the pressure differential across an inhaler in an apparatus comprising a first chamber and a second chamber; wherein said inhaler is installed in the second chamber.

14. The method of claim 12, wherein a linear regression of pressure and flow data collected at the at least three predetermined value settings results in a coefficient of determination greater than 0.9.

* * * * *